United States Patent [19]
Ogilvie et al.

[11] Patent Number: 5,776,913
[45] Date of Patent: Jul. 7, 1998

[54] THERAPEUTIC DIET FOR METABOLIC ABNORMALITIES FOUND IN ANIMALS WITH LYMPHOMA

[75] Inventors: Gregory K. Ogilvie, Ft. Collins, Colo.; Deborah J. Davenport, Lecompton, Kans.; Kathy L. Gross, Topeka, Kans.; Michael S. Hand, Maple Hill, Kans.

[73] Assignee: Colgate Palmolive Company, New York, N.Y.

[21] Appl. No.: 544,421

[22] Filed: Oct. 10, 1995

[51] Int. Cl.$^6$ .............. A61K 31/715; A61K 31/685; A61K 31/195; A61K 31/20

[52] U.S. Cl. .............. 514/57; 514/77; 514/78; 514/558; 514/560; 514/564

[58] Field of Search .............. 514/558, 560, 514/524, 57, 78, 77

[56] References Cited

FOREIGN PATENT DOCUMENTS

| | | |
|---|---|---|
| 0026985 | 4/1981 | European Pat. Off. . |
| 0567433 | 10/1993 | European Pat. Off. . |
| 0609056 | 8/1994 | European Pat. Off. . |
| 0678247 | 10/1995 | European Pat. Off. . |
| 1215245 | 8/1989 | Japan . |
| 6038708 | 2/1994 | Japan . |

OTHER PUBLICATIONS

Chemical Abstracts,vol. 114,(No. 4),Abst.No. 30,136–p.Jan. 28, 1991.

Chemical Abstracts,vol. 122,(No. 18)Abst.No. 222,894–w, May 1, 1995.

Webster's New International Dictionary of The English Language,Second Edition,p. 371,Meriam Pub., 1950.

Cancer, vol. 71, No. 10, 1993 Philadelphia, US, pp. 3146–3152, XP000617658 G.K. Ogilvie et al: "Energy Expenditure in Dogs with Lymphoma Fed Two Specialized Diets".

FASEB Journal for Experimental Biology, vol. 9, No. 4, 1995, Bethesda, Md. US, p. A863 XP002024954 S.L. Miller et al: "Low–Dose Parenteral Arginine Does Not Affect Glucose Utilization In Vivo".

Breast Cancer Research and Treatment, vol. 13, No. 1, 1989, Boston, US, pp. 49–60, XP000617654 F.S. Shofer et al: "Histopathologic and Dietary Prognostic Factors for Canine Mammary Carcinoma".

American Journal of Epidemiology, vol. 133, No. 7, 1991, Baltimore, US, pp. 694–703, XP000617669 E.G. Sonnenschein et al: "Body Conformation, Diet, and Risk of Breast Cancer in Pet Dogs: A Case–Control Study".

*Primary Examiner*—Alan L. Rotman
*Attorney, Agent, or Firm*—Paul Shapiro

[57] ABSTRACT

The severity of metabolic disturbance in animals with cancer is mitigated by feeding the animal a nutritionally balanced food composition having a fat content of about 27 to 35%, on a dry matter basis, a carbohydrate content of about 15 to about 27% on a dry matter basis in which is present a mixture of arginine, omega-3 polyunsaturated fatty acids and omega-6 polyunsaturated fatty acids, the weight ratio of omega-3, omega-6 fatty acid being in the range of 0.3:1 to 3.5:1.

9 Claims, No Drawings

THERAPEUTIC DIET FOR METABOLIC ABNORMALITIES FOUND IN ANIMALS WITH LYMPHOMA

BACKGROUND OF THE INVENTION

1. Field of the Invention

The present invention relates to a method of reducing metabolic abnormalities found in animals with cancer and including a pet food composition effective for this purpose.

2. The Prior Art

Cancer cachexia is a complex paraneoplastic syndrome of progressive involuntary weight loss that occurs even in the face of adequate nutritional intake. For example, dogs with cancer during prolonged periods of illness, notwithstanding conventional, adequate nutritional intake, undergo a significant loss of body weight. Of major concern to those in the field of pet nutrition is the loss of body mass, i.e., muscles, organs and the like. The severe weight loss and debilitative wasting of lean body mass associated with cancer complicates the treatment of the pet and contributes to a decreased quality of life, decreased response to treatment and shortened survival time.

The precise mechanism by which the cachexia syndrome in animals with cancer operates is not completely understood. Previous studies indicate significant alterations in carbohydrate metabolism, it being observed that dogs with lymphoma and other, non-hematopoietic malignancies have elevated lactate and insulin blood levels (Vail et al, J. Vet. Int. Med. 1990; 4:8–11; Ogilvie et al, Amer. J. Vet Res., in press). The increase in lactate levels is believed to be due, at least in part, to the tumors preferentially metabolizing glucose, using anaerobic glycolysis for energy, thereby forming lactate as an end product. The alteration in carbohydrate metabolism (hyperlactatemia, hyperinsulinemia) does not improve when dogs with lymphoma are put into remission with chemotherapy (doxorubicin) or in dogs with non-hematopoietic malignancies that have these tumors completely excised with surgery suggesting that tumors induce long-term changes in metabolism. (Ogilivie et al, Cancer 1992; 69: 233–238; Ogilvie et al, Amer. J. Vet Res., in press).

Despite the need for a pet food formulation which can be used for correction of metabolic abnormalities recognized in animals with cancer, no effective diet has been proposed or developed by the animal nutrition art. Thus the art continues to search for a diet for treating cachexia resulting from cancer.

SUMMARY OF THE INVENTION

The present invention is premised on the discovery that metabolic disturbances in animals with cancer can be treated by a diet having particular amounts of nutrients. By providing a patient with a diet high in fat (i.e., greater than 27% on a dry matter basis) and low in carbohydrate (i.e., no more than 27% on a dry matter basis) supplemented with arginine and polyunsaturated omega-3 and omega-6 fatty acids, the metabolic disturbance in an animal with cancer is ameliorated. The term dry matter basis when used herein means the nutrient content of the product after the moisture is removed.

DESCRIPTION OF THE PREFERRED EMBODIMENTS

The method of reducing metabolic disturbance in pet animals with cancer, particularly dogs, pursuant to the present invention, is provided by feeding the pet animal a food composition in which the nutrient content is comprised of 27 to about 35% on a dry matter basis of fat and about 15 to about 27% on a dry matter basis of carbohydrate supplemented to contain on a dry matter basis about 2.0 to about 3.5% arginine, about 2.5 to about 7.5% omega-3 fatty acids and about 2.0 to about 6.0% omega-6 fatty acids, the weight ratio of omega-3 to omega-6 fatty acids being in the range of about 0.3:1 to 3.5:1. The present invention is generally intended to apply to all forms of pet food including dry, canned or intermediate moisture pet food products, as these terms are recognized by those skilled in the art of pet food formulation and manufacturing.

The pet food composition of the present invention is not intended to be restricted by any specific listing of proteinaceous, fat or carbohydrate ingredients or product form, since these will be entirely dependent upon the nutritional balance of the ration desired as well as their availability to the pet food manufacturer. Generally, aside from the nutritionally balancing ingredients such as vitamins, minerals and the like, the pet food compositions of the present invention have a moisture content of about 10 to about 90% by weight and preferably about 65 to about 75% by weight and are formulated having a nutrient content listed in Table I below.

TABLE I

| Nutrient | Nutrient Content % (Dry Matter Basis) |
| --- | --- |
| Carbohydrate | about 15 to about 27 |
| Protein | about 35 to about 48 |
| Fat | about 27 to about 35 |
| Omega-3 Fatty Acid | about 2.5 to about 7.5 |
| Omega-6 Fatty Acid | about 2.0 to about 6.0 |
| Arginine | about 2.0 to about 3.5 |
| Nutritional balancing agents such as vitamins (A, $B_1$, $B_2$, $B_6$, E) and minerals (Ca, P, Na, K, Mg, Fe, Cl) | about 0.4 to about 1.0 |

A critical factor insofar as the present invention is the presence of arginine and omega-3 and omega-6 polyunsaturated fatty acids in a nutritionally balanced pet food composition containing the concentrations of fat and carbohydrate in the proportions specified in Table I above. It is the control of these latter two nutrients in the nutritionally balanced pet food composition in combination with the arginine and omega-3 and 6 polyunsaturated fatty acid nutrients that has been found to provide a remarkable reduction in the severity of metabolic abnormalities in dogs with cancer to which the food product is fed. The exact means or manner in which the fat and carbohydrate ingredients are controlled in the diet is not critical to the practice of the present invention and the respective levels of these particular ingredients in the pet food can be controlled primarily by selection of the ingredients based upon analysis or estimated fat and carbohydrate content in any of the ingredients used in the formulation of the pet food composition.

The specific dietary balance between fat and carbohydrates in combination with the specific concentrations of arginine, omega-3 and omega-6 polyunsaturated fatty acids set forth herein is believed to positively affect the negative impact of metabolic abnormalities in animals with cancer by providing a means for correcting such abnormalities in the animal.

The fat and carbohydrate nutrients used to prepare the pet food compositions of the present invention may be supplied by ingredients such as meat, meat by-products, other animal protein sources and grains as the food source. By meat is meant the flesh of cattle, swine, sheep, goat, horses, and other mammals as well as poultry and fish. Meat by-products include, but are not limited to lungs, kidneys, brain, livers, and stomachs and intestines freed of their contents. Additionally, meat, meat by-products, and other animal protein source mixtures are suitable for use in the pet food of this invention. The nutrient ingredients may also include amounts of cereal grains such as wheat, corn, barley and rice and fibrous bulking materials such as cellulose, beet pulp, peanut hulls or soy fiber.

A typical canned dog food product of the present invention is prepared from a mixture of the following ingredients:

| Ingredient | % by Weight |
| --- | --- |
| Water | 25–30 |
| Lungs, Beef Lobes | 40–45 |
| Liver | 6–10 |
| Chicken | 5–8 |
| Rice | 4–8 |
| Fish Oil (omega-3 and omega-6 fatty acid source) | 5–8 |
| Cellulose | 0.5–2 |
| Beet Pulp | 0.5–2 |
| Inorganic Salts (calcium carbonate, iron oxide, potassium citrate) | 0.5–2 |
| Arginine | 0.2–0.6 |
| Vitamins | 0.01–0.2 |
| Taurine | 0.02–0.2 |
| Minerals | 0.01–0.2 |

In preparing the pet food product of the present invention, the nutrient composition is adjusted so that the concentration of omega-3 polyunsaturated fatty acids is present in the animal food product of the present invention at a concentration of about 2.5 to about 7.5% on a dry matter basis and preferably about 7.0 to about 7.5% on a dry matter basis, and the omega-6 polyunsaturated fatty acid is present in the pet food product at a concentration of about 2.0 to about 6.0% on a dry matter basis and preferably about 2 to about 2.5% on a dry matter basis.

The omega-3 and omega-6 polyunsaturated fatty acids are most conveniently provided by fish oils such as menhaden, mackerel, herring, anchovy and salmon which all have significant levels of omega-3 and omega-6 polyunsaturated fatty acids. Omega-3 fatty acids C20:5 eicospentaenoic acid and C22:6 docosahexaenoic acid are typical of fish oil and together comprise about 25-38% of the fish oil. Examples of omega-6 polyunsaturated fatty acids include linoleic acid and arachidonic acid. Sources typically are animal fats and vegetable oils such as soy, canola and corn oil.

The animal food product of the present invention is supplemented with arginine to contain about 2.0 to about 3.5% on a dry matter basis and preferably about 3.0 to about 3.5% on a dry matter basis. The arginine and fish oil components of the pet food product of the present invention are incorporated in the food product during the processing of the formulation, as for example, during and after mixing of the ingredients of the pet food. Distribution of these components can be accomplished by conventional means.

Other additives may be included in this pet food as needed. These other additives include flavoring, vitamins, minerals, coloring and mixtures thereof. These additives are added for nutritional purposes and palatability. Suitable amounts are easily determined by a person having ordinary skill in the art. However, up to about 5% of these ingredients are customarily used. Ingredients in this category are exemplified by iron oxide, sodium chloride, potassium citrate, potassium chloride, and other edible salts, flavoring, vitamins, minerals and coloring.

The pet food products of the present invention are prepared by mixing ground animal and poultry proteinaceous tissues with the remaining ingredients which include fish oils, arginine, cereal grains and other nutritionally balancing ingredients and special purpose additives such as vitamin and mineral mixtures, inorganic salts, cellulose and beet pulp bulking agents and the like. Water sufficient for processing is also added. A vessel suitable for heating while blending the components is used.

Heating of the ingredient mix may be effected in any suitable manner as, for example, by direct steam injection or by using a vessel fitted with a heat exchanger. Following the addition of the last ingredient, the mixture is heated to a temperature ranging from approximately 70° to about 140° F. Temperatures outside of this range are acceptable but may not be commercially practical without the use of other processing aids. When heated to the appropriate temperature, the material is in the form of a thick liquid. The thick liquid product is then filled into cans. A lid is applied and the container is hermetically sealed. Next, the sealed can is placed into conventional equipment designed to sterilize the contents. This is usually accomplished by heating to temperatures above 230° F. for an appropriate time which is dependent on the exact temperature and formula.

For the purposes of a complete understanding of the present invention it should be recognized that the term pet food composition is generally intended to apply to commercially sold and nutritionally balanced pet food which provides the sole food intake for the pet animal.

The following Example is intended to describe specific but non-limiting embodiments of the present invention.

EXAMPLE

Preparation of Pet Food Product

A pet food product of the present invention was prepared by blending a mixture of the ingredients listed in Table II below and heating the mixture to 135° F. for 15 minutes followed by filling cans at 110° F. to form a thick liquid which was canned and sterilized at 250° F. for 83 minutes.

TABLE II

| Ingredient | Lbs. |
| --- | --- |
| Lungs, Beef | 44.00 |
| Water | 26.12 |
| Liver, Pork | 8.00 |
| Rice, Parboiled | 6.00 |
| Menhaden Oil (1) | 5.75 |
| Chicken, Mechanically Deboned | 5.50 |
| Natural Flavor* | 1.50 |
| Cellulose | 1.00 |
| Beef Pulp | 1.00 |
| Potassium Citrate | 0.50 |
| L-Arginine | 0.30 |
| Calcium Carbonate | 0.10 |
| Vitamin mix** | 0.08 |
| Mineral Mix*** | 0.05 |
| Taurine | 0.05 |
| Red Iron Oxide | 0.03 |
| Choline Chloride | 0.02 |
| Total | 100.00 |

TABLE II-continued

*Available from Applied Food Biotechnologies
**Available from Roche Animal Health and Nutrition
***Available from J. M. Huber Corp.

| (1) Fatty Acid Composition of Menhaden Oil**** Fatty Acid | Wt. % of Predominant Fatty Acids (a) |
|---|---|
| Palmitic (16:0) | 16.2% |
| Palmitoleic (16:1) | 11.6% |
| Stearic (18:0) | 2.9% |
| Oleic (18:1) | 10.9% |
| Linoleic (18:2) | 1.2% |
| Linolenic (18:3) | 1.6% |
| Octadecatetraenoic (18:4) | 3.2% |
| Eicosapentaenoic (20:5) | 14.1% |
| Docosahexaenoic (22:6) | 11.9% |
| Eicosenoic (20:1) | 1.3% |
| Arachidonic (20:4) | 1.7% |
| Docosapentaenoic (22:5) | 2.4% |

****Commercially available from Zapata Protein, Inc.
(a) Fatty acid concentrations <1% are not included Analysis of the retorted pet food product prepared from the ingredients of Table II indicated, as recorded in Table III, the presence of the following constituents:

TABLE III

A. Major Nutrients

| Nutrient | % by Weight | % Dry Matter |
|---|---|---|
| Moisture | 71.6 | NA |
| Protein | 10.8 | 37.9 |
| Fat | 9.3 | 32.7 |
| Carbohydrate | 6.0 | 21.2 |
| Fiber, crude | 1.0 | 3.5 |
| Ash | 1.3 | 4.7 |
| Calcium | 0.15 | 0.5 |
| Phosphorus | 0.14 | 0.5 |
| Sodium | 0.08 | 0.3 |
| Potassium | 0.30 | 1.1 |
| Magnesium | 0.01 | 0.04 |
| Chloride | 0.12 | 0.42 |
| Arginine | 1.0 | 3.4 |
| Omega-6 Fatty acid | 0.6 | 2.3 |
| Omega-3 Fatty Acid | 2.1 | 7.3 |

B. Minor Nutrients

| Nutrients | Units | % by weight | % Dry Matter |
|---|---|---|---|
| Copper | (mg/kg) | 1.5 | 5.3 |
| Iron | (mg/kg) | 55 | 195 |
| Manganese | (mg/kg) | 5.7 | 20 |
| Zinc | (mg/kg) | 56 | 195 |
| Selenium | (mg/kg) | 0.3 | 1.0 |
| Iodine | (mg/kg) | 0.5 | 1.6 |
| Tryptophan | % | 0.6 | 2.2 |
| Threonine | % | 0.4 | 1.4 |
| Methionine | % | 0.2 | 0.6 |
| Isoleucine | % | 0.3 | 1.2 |
| Leucine | % | 0.8 | 2.8 |
| Tyrosine | % | 0.6 | 2.1 |
| Histidine | % | 0.3 | 0.9 |
| Lysine | % | 0.7 | 2.4 |
| Taurine | % | 0.6 | 1.9 |
| Biotin | (mg/kg) | 0.1 | 0.5 |
| Choline | (mg/kg) | 1070 | 3765 |
| Folic Acid | (mg/kg) | 0.3 | 1.2 |
| Niacin | (mg/kg) | 26 | 92 |
| Pantothenic Acid | (mg/kg) | 9 | 31 |
| Riboflavin ($B_2$) | (mg/kg) | 4 | 15 |

TABLE III-continued

| Pyridoxine ($B_6$) | (mg/kg) | 3 | 10 |
|---|---|---|---|
| Vitamin $B_{12}$ | (mg/kg) | 0.1 | 0.4 |
| Thiamine ($B_1$) | (mg/kg) | 18 | 64 |
| Vitamin E | (IU/kg) | 150 | 500 |
| Vitamin A | (IU/kg) | 25000 | 85000 |

A fifteen week study on the lactate and insulin blood levels of dogs with cancer fed two different pet food compositions designated "Diet 1" and "Diet 2" was initiated with twenty-eight dogs with histologically confirmed high grade stage IIII or IVa lymphoma, according to the World Health Organization classification scheme. Dogs were excluded from the study if they were cachectic or if they had received chemotherapy, exogenous steroids, or anesthesia in the 30 days before their selection for the study. In addition, dogs with concurrent diseases such as renal failure, hepatic cirrhosis, endocrine diseases, obesity, or hypercalcemia secondary to lymphoma were excluded. Eighteen dogs were stage IIIa (generalized lymph node involvement, without systemic signs) and ten dogs were stage IVa (clinical evidence of liver and/or spleen involvement, without systemic signs). Median and mean weights of the dogs were 22 kg and 24 kg, respectively with a range from 5 kg to 30 kg. Ages of the dogs ranged from 3.5 to 13 years with a median of 7 years and a mean of 7 years.

All dogs were randomized blindly into one of two groups and exclusively fed water and either Diet 1 or Diet 2. Diet 1 was the nutritionally balanced, high fat/low carbohydrate dog food supplemented with arginine and omega-3 and omega-6 fatty acids prepared in accordance with the Example. Diet 2 was a control which had the same composition as Diet 1 except the arginine and omega-3 and omega-6 fatty acid supplements were not included in the food formulation.

To determine the effect of Diets 1 and 2 on the metabolic dysfunction of the dogs, intravenous glucose tolerance tests and diet tolerance tests were conducted. Each study was performed prior to initiation of diet therapy and cancer chemotherapy. This period is identified as the pretreatment period in Tables IV–VII. Three, 6, 9, 12 and 15 weeks following initiation of diet and cancer chemotherapy, the intravenous glucose tolerance tests and diet tolerance tests were repeated.

Intravenous Glucose Tolerance Test (IVGTT) and Concomitant Lactate and Insulin Levels Following an overnight 12 hour fast, blood was taken before and 5, 15, 30, 45, and 60 minutes following the intravenous administration of 500 mg/kg of 25% dextrose over 30 seconds. Samples were stored at −20° C. immediately after collection and assayed together at a later time. Lactate concentrations were determined on serum by a semi-automated enzymatic method (YSI Glucose, 2700 Select Lactate Analyzer, Yellow Springs, Ohio). Serum insulin concentrations were determined in duplicate by radioimmunoassay techniques with a commercially available kit (Catalog #07-160102, ICN Biomedicals Inc., Carcon, Calif.).

Diet Tolerance Test (DTT) and Concomitant Lactate and Insulin Levels

Following an overnight 12 hour fast, blood was taken before, immediately after, and 5, 15, 30, 45, 60, 90, 120, 180, 240, 300, and 360 minutes after dogs were allowed to consume either Diet 1 or Diet 2, that they were randomized to receive. The amount fed was calculated as ½[70 (body weight$_{kg}^{0.75}$)]. Samples were taken for analysis of lactate and insulin. Samples were stored at −20° C. immediately after collection and assayed together at a later time. Lactate and insulin were determined as described above.

The results of the IVGTT and DTT tests are summarized in Tables IV–VII below. In these Tables the terms "Diet 1" and "Diet 2" mean the dogs fed Diet 1 and Diet 2 in the 15 week study.

The results recorded in Tables IV through VII show the effectiveness of the incorporation of arginine and omega-3 and omega-6 polyunsaturated fatty acids in a high fat/low carbohydrate pet food fed to dogs with cancer to mitigate metabolic disturbance.

For example, in the IVGTT, lactate and insulin concentrations normalize in the Diet 1 group. More specifically, the lactate and insulin concentrations significantly decrease in the dogs fed Diet 1, but not in the Diet 2 (control) group compared to pre-treatment values. The development of elevated lactate and insulin concentrations in response to a glucose challenge is substantially reduced in the Diet 1 group when compared to the Diet 2 group.

In the Diet Tolerance Test, the data are exactly as described above for intravenous glucose tolerance testing. Dogs fed Diet 1 normalized lactate and insulin levels and produced less lactate and insulin in response to the diet challenge as compared to dogs fed Diet 2.

TABLE IV

Glucose Tolerance Test
Lactate in Plasma (mg/dl)

| Test Period | | 0 | 5 | 15 | 30 | 45 | 60 |
|---|---|---|---|---|---|---|---|
| Pre-Treatment* | Diet 1a | 15 | 15 | 18 | 17 | 15 | 14 |
| | Diet 2 | 13 | 14 | 17 | 19 | 11 | 15 |

TABLE IV-continued

Glucose Tolerance Test
Lactate in Plasma (mg/dl)

| Test Period | | 0 | 5 | 15 | 30 | 45 | 60 |
|---|---|---|---|---|---|---|---|
| Post-Treatment** | | | | | | | |
| 3 weeks | Diet 1b | 9 | 9 | 10 | 11 | 10 | 9 |
| | Diet 2 | 10 | 11 | 13 | 16 | 15 | 13 |
| 15 weeks | Diet 1b | 9 | 8 | 10 | 10 | 9 | 7 |
| | Diet 2 | 11 | 12 | 13 | 17 | 15 | 12 |

*Prior to Initiation of diet and cancer treatment.
**Weeks following initiation of diet and cancer treatment
a,b Dogs fed Diet 1 had significantly different serum lactate values at all time points at 3 and 15 weeks post-treatment.

TABLE V

Glucose Tolerance Test
Insulin in Plasma (uU/dl)

| Test Period | | 0 | 5 | 15 | 30 | 45 | 60 |
|---|---|---|---|---|---|---|---|
| Pre-Treatment* | Diet 1a | 24a | 98a | 112a | 58 | 36a | 27a |
| | Diet 2 | 28 | 71 | 86 | 55 | 34 | 28 |
| Post-Treatment** | | | | | | | |
| 3 weeks | Diet 1 | 21 | 83b | 93 | 53 | 22b | 18b |
| | Diet 2 | 26 | 82 | 100 | 64 | 44 | 24 |
| 15 weeks | Diet 1 | 14 | 87 | 87b | 56 | 21b | 14b |
| | Diet 2 | 26 | 82 | 100 | 64 | 44 | 24 |

*Prior to initiation of diet and cancer treatment.
**Weeks following initiation of diet and cancer treatment.
a,b Dogs fed Diet 1 had significantly different serum insulin values at 5, 45 and 60 minutes at 3 weeks post-treatment and 0, 15, 45, and 60 minutes at 15 weeks post-treatment compared to pretreatment.

TABLE VI

Diet Tolerance Test
Lactate In Plasma (mg/dl)

| Test Period | Group | 0 | 5 | 15 | 30 | 45 | 60 | 90 | 120 | 180 | 240 | 300 | 360 |
|---|---|---|---|---|---|---|---|---|---|---|---|---|---|
| Pre-Treatment | Diet 1a | 12.9 | 12.9 | 13.3 | 13.4 | 13.8 | 13.5 | 14.0 | 13.8 | 12.2 | 10.6 | 9.1 | 9.1 |
| | Diet 2 | 13.4c | 13.4 | 15.1c | 14.1c | 14.1c | 14.9 | 16.1 | 14.0 | 12.1 | 11.1 | 9.9 | 9.7c |
| Post-Treatment** | | | | | | | | | | | | | |
| 3weeks | Diet 1 | 7.6 | 7.0 | 7.2 | 8.3 | 8.6 | 8.8 | 8.8 | 7.5 | 6.3 | 4.9 | 4.7 | 4.1 |
| | Diet 2 | 11.7 | 10.9 | 11.8 | 12.9 | 14.8 | 15.4 | 15.2 | 15.3 | 10.2 | 7.7 | 6.8 | 6.1 |
| 6 weeks | Diet 1b | 8.9 | 7.1 | 8.0 | 8.6 | 10.3 | 10.1 | 8.8 | 8.3 | 6.1 | 5.1 | 4.4 | 4.3 |
| | Diet 2 | 9.7 | 10.3 | 10.3 | 11.5 | 14.2 | 15.5 | 14.4 | 13.0 | 10.7 | 8.5 | 7.1 | 6.3 |
| 9 weeks | Diet 1b | 6.4 | 6.1 | 9.0 | 7.7 | 7.9 | 8.3 | 8.6 | 7.7 | 5.5 | 4.5 | 4.5 | 5.2 |
| | Diet 2 | 11.1 | 10.9 | 10.7 | 12.2 | 14.5 | 14.8 | 14.2 | 14.6 | 10.8 | 8.6 | 7.2 | 6.5 |
| 12 weeks | Diet 1b | 6.3 | 5.7 | 6.0 | 6.8 | 7.4 | 7.9 | 8.7 | 8.0 | 5.8 | 5.3 | 4.6 | 4.4 |
| | Diet 2 | 10.6d | 10.2 | 9.7d | 10.4d | 11.6d | 13.8 | 16.0 | 12.3 | 10.3 | 8.4 | 8.1 | 6.5d |

*Prior to initiation of diet and cancer treatment.
**Weeks following initiation of diet and cancer treatment.
a,b Dogs fed Diet 1 had significantly different serum lactate values across all time points at 6, 9, & 12 weeks post-treatment compared to pre-treatment.
c,d Dogs fed Diet 2 had significantly different serum lactate values at 0, 15, 30, 45, and 360 minutes at 12 weeks compared to pretreatment.

TABLE VII

Diet Tolerance Test
Insulin in Plasma (μU/dl)

| Test Period | Group | Minutes after Feeding | | | | | | | | | | | |
|---|---|---|---|---|---|---|---|---|---|---|---|---|---|
| | | 0 | 5 | 15 | 30 | 45 | 60 | 90 | 120 | 180 | 240 | 300 | 360 |
| Pre-Treatment* | Diet 1 | 58 | 36a | 37 | 38 | 41 | 35 | 34 | 42 | 38 | 39a | 34 | 37 |
| | Diet 2 | 65 | 41 | 38 | 31 | 32c | 41 | 26 | 32 | 25c | 29 | 30 | 29 |
| Post-Treatment** | | | | | | | | | | | | | |
| 3 weeks | Diet 1 | 32 | 24b | 23 | 25 | 27 | 28 | 26 | 27 | 23 | 26b | 25 | 27 |
| | Diet 2 | 54 | 40 | 35 | 35 | 40 | 37 | 38 | 27 | 33 | 44 | 32 | 23 |
| 6 weeks | Diet 1 | 20 | 26b | 31 | 26 | 25 | 25 | 24 | 23 | 28 | 27b | 28 | 28 |
| | Diet 2 | 53 | 23 | 26 | 26 | 35 | 31 | 34 | 33 | 32 | 27 | 29 | 29 |
| 9 weeks | Diet 1 | 25 | 23b | 26 | 28 | 28 | 32 | 29 | 28 | 27 | 27b | 28 | 28 |
| | Diet 2 | 72 | 31 | 26 | 33 | 44d | 34 | 26 | 41 | 42d | 25 | 33 | 30 |
| 12 weeks | Diet 1 | 29 | 29b | 28 | 26 | 27 | 25 | 26 | 27 | 27 | 30b | 29 | 29 |
| | Diet 2 | 56 | 34 | 43 | 42 | 34 | 46 | 45 | 38 | 47 | 43 | 31 | 31 |

*Prior to initiation of diet and cancer treatment.
**Weeks following initiation of diet and cancer treatment.
a,b Dogs fed Diet 1 had significantly different serum insulin values at 5 and 240 minutes at 3, 6, 9, & 12 weeks compared to pretreatment.
c,d Dogs fed Diet 2 had significantly different serum insulin values at 45 and 180 minutes at 9 weeks compared to pretreatment.

What is claimed is:

1. A method for mitigating the severity of metabolic disturbances in animals with cancer cachexia associated with lymphoma comprising (a) forming a nutritionally balanced petfood composition having a fat content of about 27 to 35% on a dry matter basis, a carbohydrate content of about 15 to about 27% on a dry matter basis in which is also present a mixture of arginine, omega-3 polyunsaturated fatty acids and omega-6 polyunsaturated fatty acids, and (b) feeding the composition to the animal with cancer.

2. The method of claim 1 wherein arginine is present in the food composition at a concentration of about 2.0 to about 3.5% on a dry matter basis.

3. The method of claim 1 wherein the omega-3 polyunsaturated fatty acid is present in the food composition at a concentration of about 2.5 to about 7.5% on a dry matter basis.

4. The method of claim 1 wherein the omega-6 polyunsaturated acid is present in the food composition at a concentration of about 2.0 about 6.0% on a dry matter basis.

5. The method of claim 1 wherein the weight ratio of omega-3 polyunsaturated fatty acid to omega-6 fatty acids is about 0.3:1–3.5:1.

6. A therapeutic composition for mitigating the severity of metabolic disturbance in animals with cancer cachexia associated with lymphoma comprising (a) a nutritionally balanced food having a fat content of about 27 to 35% on a dry matter basis, a carbohydrate content of about 15 to about 27% on a dry matter basis in which is present a mixture of arginine, omega-3 polyunsaturated fatty acids and omega-6 polyunsaturated fatty acids, the weight ratio of omega-3 to omega-6 fatty acid being in the range of about 0.3:1 to 3.5:1.

7. The composition of claim 6 wherein arginine is present in the food composition at a concentration of about 2.0 to about 3.5% on a dry matter basis.

8. The composition of claim 6 wherein the omega-3 polyunsaturated fatty acid is present in the food composition at a concentration of about 2.5 to about 7.5% by on a dry matter basis.

9. The composition of claim 6 wherein the omega-6 polyunsaturated acid is present in the food composition at a concentration of about 2.0 to about 6.0% by on a dry matter basis.

* * * * *

UNITED STATES PATENT AND TRADEMARK OFFICE
CERTIFICATE OF CORRECTION

PATENT NO. : 5,776,913
DATED : July 7, 1998
INVENTOR(S) : Gregory K. Ogilvie, et al It is certified that error appears in the above-indentified patent and that said Letters Patent is hereby corrected as shown below:

On the title page, item [73] Assignee, insert the following:

Colorado State University Research Foundation,
Fort Collins, Colorado

Signed and Sealed this

Ninth Day of November, 1999

Attest:

Q. TODD DICKINSON

*Attesting Officer*        *Acting Commissioner of Patents and Trademarks*